United States Patent [19]
Nedberge et al.

[11] Patent Number: 4,816,258
[45] Date of Patent: Mar. 28, 1989

[54] TRANSDERMAL CONTRACEPTIVE FORMULATIONS

[75] Inventors: Diane E. Nedberge, Los Altos; Patricia S. Campbell, Palo Alto; Robert M. Gale; Su I. Yum, Los Altos, all of Calif.

[73] Assignee: ALZA Corporation, Palo Alto, Calif.

[21] Appl. No.: 19,163

[22] Filed: Feb. 26, 1987

[51] Int. Cl.⁴ .............................................. A61K 13/02
[52] U.S. Cl. ................................... 424/448; 424/449; 424/DIG. 14; 514/841; 514/874
[58] Field of Search ............... 424/448, 449, DIG. 14; 514/846, 874

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,710,795 | 1/1973 | Higuchi et al. | 128/260 |
| 3,948,262 | 4/1976 | Zaffaroni | 128/260 |
| 4,144,317 | 3/1979 | Higuchi et al. | 424/21 |
| 4,286,592 | 9/1981 | Chandrasekaran | 128/260 |
| 4,291,014 | 9/1981 | Keith et al. | 424/28 |
| 4,314,557 | 2/1982 | Chandrasekaran | 128/260 |
| 4,335,115 | 6/1982 | Thompson et al. | 424/181 |
| 4,379,454 | 4/1983 | Campbell et al. | 604/897 |
| 4,438,139 | 3/1984 | Keith et al. | 424/28 |
| 4,568,343 | 2/1986 | Leeper et al. | 604/896 |
| 4,624,665 | 11/1986 | Nuwayser | 604/307 |

FOREIGN PATENT DOCUMENTS

0013606-B1 7/1980 Fed. Rep. of Germany .
0013606-A2 7/1980 United Kingdom .

OTHER PUBLICATIONS

Näthke, I., Heller, J. and Baker, R. W., "Transdermal Delivery of Levonorgestrel" published in Proceedings of the 13th International Symposium on Controlled Release of Bioactive Materials (Chaudry, I. and Thies, C. Editors, the Controlled Release Society, Inc.) at pp. 29–30 (1986).

Primary Examiner—Thurman K. Page
Attorney, Agent, or Firm—Edward L. Mandell; Shelley G. Precivale; Steven F. Stone

[57] ABSTRACT

A transdermal delivery system for the administering of ethinyl estradiol and levonorgestrel, in combination, utilizing a polymer matrix having the drug formulation along with a permeation enhancer dispersed throughout.

26 Claims, 1 Drawing Sheet

TRANSDERMAL CONTRACEPTIVE FORMULATIONS

BACKGROUND OF THE INVENTION

Field of the Invention

This invention relates to transdermal drug delivery. More particularly, this invention relates to contraceptive delivery and still more particularly, but without limitation thereto, this invention relates to the transdermal delivery of ethinyl estradiol and levonorgestrel, in combination, at therapeutically effective rates.

Related Patent Applications

This invention is related to the inventions disclosed in the copending, coassigned patent applications of Gale, et al for Transdermal Administration of Progesterone, Estradiol Esters and Mixtures Thereof, of Cheng, et al for Skin Permeation Enhancer Compositions using Glycerol Monolaurate, and for Cheng, et al for Skin Permeation Enhancer Compositions, all of like date herewith.

Description of the Prior Art

The transdermal route of parenteral delivery of drugs provides many advantages and transdermal systems for delivering a wide variety of drugs or other beneficial agents are described in U.S. Pat. Nos. 3,598,122, 3,598,123, 4,379,454, 4,286,592, 4,314,557 and 4,568,343, for example, all of which are incorporated herein by reference.

Oral combination pills and intrauterine devices for purposes of contraception have been well documented for their problems such as inconvenience and side effects. Transdermal delivery of contraceptives as disclosed herein, is an attempt to eliminate or reduce those problems.

SUMMARY OF THE INVENTION

An object of the present invention is to provide delivery of contraceptives by means of transdermal systems.

A further object is to co-administer ethinyl estradiol and levonorgestrel at contraceptively effective rates.

A still further object of the present invention is to deliver contraceptives transdermally using skin permeation enhancers such as glycerol monooleate.

An even further object is to provide a method for the transdermal administration of ethinyl estradiol and levonorgestrel, in combination.

These and other objects have been demonstrated by the present invention wherein a transdermal system is designed using a polymer matrix containing glycerol monooleate as a permeation enhancer and ethinyl estradiol and levonorgestrel, in combination, as a contraceptive formulation.

BRIEF DESCRIPTION OF THE DRAWING

The invention will be described in further detail with reference to the accompanying drawings wherein.

DESCRIPTION OF THE PREFERRED EMBODIMENT

This invention utilizes principles of transdermal drug delivery to provide a novel system for effectively administering contraceptives. Of particular significance is the use of a codelivered permeation enhancer, glycerol monooleate (GMO), to aid in drug delivery across the skin. The present invention provides continuous co-administration of ethinyl estradiol and levonorgestrel for up to seven days. GMO is used as a suitable permeation enhancer.

Figure 1:
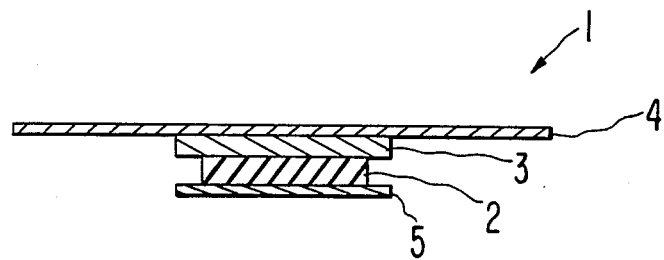
FIG. 1 is a cross-sectional view of one embodiment of the transdermal drug delivery system according to this invention.

Referring now to FIG. 1, a transdermal therapeutic system 1 according to this invention is shown which comprises a drug/permeation enhancer reservoir 2 in the form of a matrix containing the drug formulation and the permeation enhancer. The reservoir 2 is covered by an impermeable backing 3 which is preferably sized slightly larger in circumference than reservoir 2. Means 4 for maintaining the system 1 on the skin may either be fabricated together with or provided separately from the remaining elements of the system, which means in the embodiment of FIG. 1 takes the form of an adhesive overlay. The use of an adhesive overlay with this invention is preferred to the use of an in-line adhesive applied to the skin proximal surface of reservoir 2 because glycerol monoleate adversely affects the adhesive properties of most pharmaceutically acceptable contact adhesives. For this reason, impermeable backing layer 3 is preferably sized slightly larger than the reservoir 2 to provide a peripheral area around reservoir 2, free of any glycerol monoleate adjuvant, to prevent adverse interaction between the adhesive in the overlay 4 and any of the enhancer which may seep from under the base of reservoir 2 in use. A strippable release liner 5, adapted to be removed prior to application would normally be included in the packaged product.

Various materials suited for the fabrication of the various layers are disclosed in the aforementioned patents.

The polymer matrix is preferably anhydrous and suitable materials include, without limitation, natural and synthetic rubbers or other polymeric material, thickened mineral oil or petroleum jelly, for example. The preferred embodiment according to this invention is fabricated from an ethylene vinylacetate (EVA) copolymer of the type described in U.S. Pat. No. 4,144,317, preferably those having a vinylacetate (VA) content in the range of about 28 to 60% VA. Particularly good results have been obtained using 40% vinylacetate content (EVA 40).

A preferred embodiment is basically a monolith having the following composition by weight: 20–50% polymer, 10–50% tackifier, 0.01–1% ethinyl estradiol, 0.1–5% levonorgestrel and 10–50% permeation enhancer.

The preferred system uses the EVA polymer as the elastomer. Typical suitable tackifiers are fully hydrogenated aromatic hydrocarbon resins. Successful results have been achieved with use of the Hercules, Inc. (Wilmington, Delaware) product line sold under the trade name Staybelite Ester TM. Specifically, Staybelite Ester #5 and #10 have been used.

The drugs are preferably dispersed through the matrix at a concentration in excess of saturation, i.e. at unit activity. The amount of excess is determined by the intended useful life of the system. The drugs, however, may be present at initial levels below saturation without departing from this invention. The permeation enhancer, preferably GMO, is dispersed through the matrix, preferably at a concentration sufficient to provide permeation enhancing concentrations of GMO in the reservoir throughout the anticipated administration time.

Figure 2:
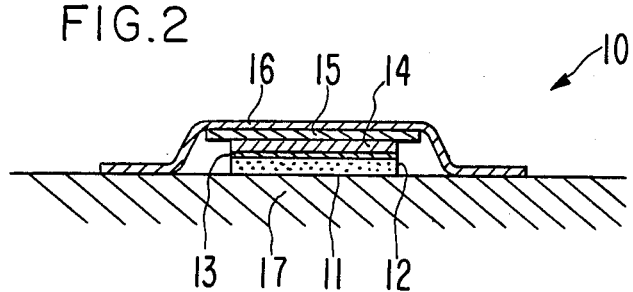
FIG. 2 is a cross-sectional view of another embodiment of the transdermal drug delivery system of this invention.

Referring now to FIG. 2, another embodiment of the invention is shown in place upon the skin 17 of a patient. In this embodiment the transdermal therapeutic system 10 comprises a multilaminate drug formulation/enhancer reservoir 11 having at least two zones 12 and 14. Zone 12 consists of a drug reservoir substantially as described with respect to FIG. 1. Zone 14 comprises a permeation enhancer reservoir which is preferably made from substantially the same matrix as is used to form zone 12 and which is substantially free of any undissolved drug. A rate-controlling membrane for controlling the release rate of the GMO from zone 12 to the skin may also be utilized between zones 12 and 14 if desired. Suitable rate-controlling membranes may be formed from polymers having a permeability to GMO lower than that of zone 12.

An advantage of the system described in FIG. 2 is that the drug loaded zone 12 is concentrated at the skin surface rather than throughout the entire mass of the reservoir. This functions to reduce the amount of drug in the system while maintaining an adequate permeation enhancer supply.

Superimposed over the drug formulation/enhancer reservoir 11 is an impermeable backing 15 and adhesive overlay 16 as described above with respect to FIG. 1. In addition, a strippable release liner (not shown) would preferably be provided on the system prior to use as described with respect to FIG. 1 and removed prior to application to the skin 17.

In the embodiments of FIGS. 1 and 2, the carrier or matrix material has sufficient viscosity to maintain its shape without oozing or flowing. If the matrix or carrier is a low viscosity flowable material, the composition can be fully enclosed in a pouch or pocket between the impermeable backing and a permeable or microporous skin contacting membrane, as known to the art from U.S. Pat. No. 4,379,454, noted above, for example.

The transdermal therapeutic systems of this invention may be fabricated by state of the art methods such as solution casting and melt blending. The main design criteria is that the active (drug formulation containing) layer be about 5–10 mils thick.

The required transdermal flux for effective contraception as provided by this invention, is at least 15 μg/day of ethinyl estradiol and at least 50 μg/day of levonorgestrel. For a 20 cm² system, these daily flux values translate to be at least 0.04 g/cm²/hr for ethinyl estradiol and at least 0.14 μg/cm²/hr for levonorgestrel.

The systems of this invention can be designed to effectively deliver ethinyl estraiiol and levonorgestrel for an extended time period of up to 7 days. The drug delivery must be continuous in order to provide effective contraception. Therefore, when one system has been in place on the skin for its effective time period, it is replaced with a fresh system. For example, for a 7 day system maintenance would involve replacing the system every 7 days with a fresh system and continuing said replacement for as long as contraception was desired.

The embodiments and applications of this invention are best understood in light of the following examples.

EXAMPLE I

A transdermal therapeutic system as described with respect to FIG. 1 for the administration of ethinyl estradiol and levonorgestrel was formulated from: 5% levonorgestrel, 0.5% ethinyl estradiol, 37.8% EVA 40, 26.6% Staybelite Ester #5 and 30.1% GMO. The in vitro skin flux was measured over a seven day period, at 37° C. The following table shows the flux data (averaged for thirteen samples) for both drugs and GMO:

TABLE I

| DAY | FLUX, μg/cm²/hr | | | | | | |
|---|---|---|---|---|---|---|---|
| | 1 | 2 | 3 | 4 | 5 | 6 | 7 |
| Ethinyl estradiol | 0.137 | 0.181 | 0.194 | 0.204 | 0.160 | 0.174 | 0.165 |
| Levonorgestrel | 0.125 | 0.166 | 0.170 | 0.190 | 0.191 | 0.211 | 0.211 |
| GMO | 101.9 | 5.4 | 4.6 | 4.0 | 4.6 | 6.9 | 9.5 |

EXAMPLE II

The transdermal (in vivo) fluxes of ethinyl estradiol and levonorgestrel were estimated, based upon the following relationships:

$$Q_{drug} = Q_{GMO} \times L_{drug} \text{ for } L < S$$

and $$Q_{drug} = Q_{GMO} \times S_{drug} \text{ for } L < S$$

where
Q = cumulative amount permeated
L = amount of drug loading in the formulation
S = drug solubility in GMO Therefore, since the Q value for GMO is 5 mg/cm² ($5 \times 10^{-3}$ g/cm²) over a seven day period, and the amount of ethinyl estradiol and levonorgestrel loaded is $5 \times 10^3$ μg/g each, the amount of each drug which permeates the skin is:

$$(5 \times 10^{-3})(5 \times 10^3) = 25 \text{ μg/cm}^2.$$

This invention has been described in detail with particular reference to certain preferred embodiments thereof, but it will be understood that variations and modifications can be effected within the spirit and scope of the invention.

What is claimed is:

1. A composition of matter for the transdermal administration of a drug formulation comprised of ethinyl estradiol and levonorgestrel, comprising a matrix containing said drug formulation and a skin permeation enhancing amount of glycerol monooleate.

2. The composition of claim 1 wherein said ethinyl estradiol is present in an amount in excess of its saturation concentration in the matrix.

3. The composition of claim 1 wherein said levonorgestrel is present in an amount in excess of its saturation concentration in the matrix.

4. The composition of claim 1 wherein said matrix comprises an ethylene vinylacetate co-polymer.

5. The composition of claim 4 wherein said ethylene vinylacetate co-polymer comprises about 28 to 60% vinylacetate.

6. The composition of claim 5 wherein said ethylene vinylacetate co-polymer comprises about 40% vinylacetate.

7. A transdermal therapeutic system comprising a reservoir containing a drug formulation comprised of ethinyl estradiol and levonorgestrel, and a skin permeation enhancing amount of glycerol monooleate, in combination with:

an occlusive backing behind the skin distal surface of said reservoir composition; and means for maintaining said reservoir composition in drug formulation and glycerol monooleate transferring relationship to human skin.

8. A method for the transdermal administration of a drug formulation comprised of ethinyl estradiol and levonorgestrel, which comprises placing said drug formulation in drug transmitting relationship to the skin in the presence of a drug permeation enhancing amount of glycerol monooleate.

9. The method of claim 8 wherein said ethinyl estradiol is at unit activity.

10. The method of claim 8 wherein said levonorgestrel is at unit activity.

11. The method of claim 8 wherein said ethinyl estradiol is delivered through the skin at a rate of at least 15 μg/day for an extended period of time.

12. The method of claim 8 wherein said levonorgestrel is delivered through the skin at a rate of at least 50 μg/day for an extended period of time.

13. A medical device for the transdermal delivery of a drug formulation comprised of ethinyl estradiol and levonorgestrel, comprising in combination:

a reservoir means containing a skin permeable formulation containing said drug formulation;

an occlusive backing behind the skin distal surface of said reservoir means and extending beyond the periphery of said reservoir means; and an adhesive overlay disposed on the skin distal surface of said occlusive backing and extending beyond the periphery thereof.

14. A medical device for the transdermal administration of a drug formulation comprised of ethinyl estradiol and levonorgestrel through intact skin for an extended period of time at a therapeutic rate of at least 15 μg/day of ethinyl estradiol and at least 50 μg/day of levonorgestrel, which comprises:

a unit activity reservoir of a skin permeable form of said formulation, said reservoir comprising a carrier having said formulation substantially uniformly distributed there through at a concentration above saturation;

a reservoir of a skin permeation enhancer for said material; and means for maintaining said formulation reservoir and said permeation enhancer reservoir in formulation and permeation enhancer transferring relationship to the same area of intact skin.

15. The medical device of claim 14 wherein said permeation enhancer reservoir is combined with said formulation reservoir.

16. The medical device of claim 14 wherein said permeation enhancer is glycerol monooleate.

17. The medical device of claim 14, further comprising a means for controlling the release of permeation enhancer from said enhancer reservoir to said formulation reservoir, said formulation reservoir being disposed between said rate controlling means and the skin.

18. The medical device of claim 14, wherein said permeation enhancer is glycerol monooleate and said formulation reservoir contains said formulation at a concentration above saturation in an amount sufficient to maintain the concentration of said formulation at least at the saturation level throughout said period.

19. The medical device of claim 14, further comprising an impermeable backing on the skin distal side of said reservoir.

20. A method for the transdermal delivery of a drug formulation comprised of ethinyl estradiol and levonorgestrel at a therapeutic rate of at least 15 μg/day of ethinyl estradiol and at least 50 μg/day of levonorgestrel, for an extended period of time, which comprises:

contacting an area of intact skin with a source of a skin permeable form of said formulation at unit activity and a skin permeation enhancer for said formulation at a permeation enhancing concentration;

maintaining said source in formulation and permeation enhancer transmitting contact with the skin for said extended period of time; and maintaining the source of said formulation at unit activity and said permeation enhancer at a permeation enhancing concentration for said extended period of time.

21. A method for producing a contraceptive effect in the human female which comprises transdermally co-administering ethinyl estradiol and levonorgestrel at contraceptively effective rates and maintaining said co-administration continuously throughout the period for which contraception is required.

22. The method of claim 21 wherein said maintenance comprises placing a transdermally therapeutic system in ethinyl estradiol and levonorgestrel transmitting relationship to human skin for an extended period of time.

23. The method of claim 22 wherein said extended period of time is the effective life of said system.

24. The method of claim 23 wherein said effective life is up to 7 days.

25. The method of claim 22 wherein said maintenance further comprises replacing said system with a second system after said extended period of time.

26. The method of claim 25 wherein said replacement is carried on repeatedly throughout the period for which contraception is desired.

* * * * *

UNITED STATES PATENT AND TRADEMARK OFFICE
CERTIFICATE OF CORRECTION

PATENT NO. : 4,816,258

DATED : March 28, 1989

INVENTOR(S) : Diane E. Nedberge, Patricia S. Campbell, Robert M. Gale, Su I. Yum It is certified that error appears in the above-identified patent and that said Letters Patent is hereby corrected as shown below:

Column 1, line 19, after Thereof, insert --U.S. Serial No. 07/019,162;-- column 1, line 22, after Monolaurate, insert --U.S. Pat. No. 4,746,515-- column 1, line 23, after Compositions insert --Using Sucrose Esters, U.S. Serial No. 07/019,442--. Column 2, line 62 "TM" should be superscripted. Column 3, line 53, before $g/cm^2$ insert --$\mu$--; line 57 delete "estraiiol", insert --estradiol--.

Signed and Sealed this

Eighth Day of May, 1990

Attest:

HARRY F. MANBECK, JR.

Attesting Officer

Commissioner of Patents and Trademarks